United States Patent
Michael et al.

(10) Patent No.: US 6,326,619 B1
(45) Date of Patent: Dec. 4, 2001

(54) CRYSTAL PHASE IDENTIFICATION

(75) Inventors: Joseph R. Michael; Raymond P. Goehner; Max E. Schlienger, all of Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/299,940

(22) Filed: Apr. 26, 1999

Related U.S. Application Data

(60) Provisional application No. 60/091,381, filed on Jul. 1, 1998.

(51) Int. Cl.[7] .................................................. H01J 37/26
(52) U.S. Cl. .............................. 250/310; 250/307
(58) Field of Search ........................... 250/310, 306, 250/307

(56) References Cited

U.S. PATENT DOCUMENTS

| | | | |
|---|---|---|---|
| 4,990,779 | * 2/1991 | Yoshitomi et al. | 250/310 |
| 5,095,207 | * 3/1992 | Tong | 250/306 |
| 5,227,630 | * 7/1993 | Saldin et al. | 250/307 |
| 5,466,934 | 11/1995 | Adams et al. | 250/307 |
| 5,557,104 | 9/1996 | Field et al. | 250/307 |

OTHER PUBLICATIONS

Goehner, R.P. and Michael, J.R., "Phase Identification in a Scanning Electron Microscope Using Backscattered Electron Kikuchi Patterns," J. Res. Natl. Inst. Stand. Technol., 1996, 101(3), 301–308.

* cited by examiner

*Primary Examiner*—Bruce Anderson
(74) *Attorney, Agent, or Firm*—Elmer A. Klavetter

(57) ABSTRACT

A method and apparatus for determining the crystalline phase and crystalline characteristics of a sample. This invention provides a method and apparatus for unambiguously identifying and determining the crystalline phase and crystalline characteristics of a sample by using an electron beam generator, such as a scanning electron microscope, to obtain a backscattered electron Kikuchi pattern of a sample, and extracting crystallographic and composition data that is matched to database information to provide a quick and automatic method to identify crystalline phases.

15 Claims, 2 Drawing Sheets

CRYSTAL PHASE IDENTIFICATION

This application claims the benefit of U.S. Provisional Application No. 60/091,381, filed on Jul. 1, 1998.

This invention was made with Government support under Contract No. DE-AC04-94AL85000 awarded by the Department of Energy. The Government has certain rights in the invention.

BACKGROUND OF THE INVENTION

The present invention generally relates to materials science and more particularly to an apparatus and method for the identification of the crystalline phase of a crystalline sample and subsequent determination of its crystallographic characteristics.

The physical properties and characteristics of crystalline materials are strongly determined by the arrangement of atoms within the compound or compounds that make up the bulk material. Often, there are many compounds that have the same chemical composition but different crystal structures and will behave differently (e.g. $TiO_2$ which can exist as three different crystal structures, each having entirely different physical properties). Thus, in order to predict a materials response or behavior, it is important to know the crystal phases that are present.

Although there are only seven basic crystal types, there are over 100,000 different crystal phase variations. If known, the crystal phase of a material provides structural parameters and geometrical relationships necessary for the determination of other material properties. Thus, the crystal phase is an important characteristic of a material that can be valuable.

Generally, for unambiguous phase identification, analysts have needed to resort to very expensive instruments whose sample preparation requirements necessitated the destruction of the sample. These techniques used by these instruments include micro X-ray diffraction (MXRD) and transmission electron microscopy (TEM). Unfortunately, MXRD is a technique that has a limited spatial resolution (>30 micrometers) or requires a synchrotron for higher resolution. Also, MXRD does not form spatial images of the sample so that the spatial relationship of various phases may be visualized. TEM is not limited by resolution like MXRD. The spatial resolution of the TEM is less than 0.1 micrometers and can form images of the material at this resolution or higher so that the spatial relationship between various constituents of the microstructure may be visualized. The great disadvantage to the TEM technique is the extensive and difficult specimen preparation that must be performed and the manual indexing of the diffraction patterns that must be performed. These two disadvantages make TEM a more time consuming and expensive technique. These systems are optimized for texture mapping. These instruments have also required long analysis times (generally several hours) and considerable expertise to provide phase identification. These instruments are also costly, requiring hundreds of thousands of dollars in investment in the capital equipment along with the costs associated with labor for analysis of the data. If the phase to be analyzed existed mainly on the surface of a component, even these more expensive alternatives have been unlikely to produce positive results.

Therefore, for many applications, crystal lattice planes and crystalline phases are typically identified by a procedure known as crystal indexing. For example, a crystal phase identify is typically assumed when performing crystal indexing processes. Given the identity of the crystal phase, mathematical relationships required to calculate the crystal indices are selected. However, many polycrystalline materials have more than one distinct crystal phase. In addition, other materials may have an unknown phase or an unknown combination of phases. Thus, an indexing solution for such a material may be incomplete or erroneous without a proper identification of the crystal phase or phases within the particular specimen.

Automated crystal indexing procedures have enabled researchers, material processors, and manufacturers to obtain valuable microstructure information over a relatively large material area. Generally, such a procedure repetitively bombards selected points of a material specimen with a beam of electrons. The electrons interact with a small volume of the material sample at the selected points, and diffracting crystals cause electron backscatter diffraction patterns or backscattered electron Kikuchi patterns (BEKPs) to form on a screen near the specimen. The BEKPs may be imaged through a video camera and digitized for further processing.

Good-quality BEKPs include a number of intersecting, relatively high intensity bands that are usually referred to as Kikuchi bands or lines. The Kikuchi bands result from electrons being diffracted from various planes in the crystal lattice at the point of bombardment. Goehner and Michael (Goehner, R. P. and Michael, J. R., J. of Research of the NIST, 101, 3, 1996) describe a scanning electron microscope (SEM) with a charge coupled device based detector to permit BEKPs to be collected. An abundance of microstructure information, including the crystal indexing solution, may be obtained by analyzing the various parameters of the Kikuchi bands. Computer-implemented image processing techniques have been developed to analyze Kikuchi bands from BEKPs taken at numerous points on a material sample and to generate displays of the specimen that convey microstructure information.

One tool used to examine microphases is the scanning electron microscope (SEM), an instrument which uses an electron beam to examine materials (from insects to computer chips) at very high magnifications, allowing examination of individual features as small as $\frac{1}{1000}$ the diameter of a human hair. SEMs allow determination of the elements present in these tiny regions of a sample, but do not allow unambiguous identification of the crystalline phase those elements comprised.

Adams, Dingley, and Field (U.S. Pat. No. 5,466,934, issued on Nov. 14, 1995) describe an apparatus using an SEM to characterize crystalline defects by comparing backscatter images of a sample with a baseline to detect the defects. The apparatus and method do not, however, determine the crystalline phase of the sample but only defects in the crystalline phase.

Field and Dingley (U.S. Pat. No. 5,557,104, issued on Sep. 17, 1996) describe an apparatus and technique for determining the crystallographic characteristics of a specimen. Field and Dingley use a conventional processing technique utilizing a computational iteration scheme to determine the resultant crystal indexing solution. The indexing solution is calculated a number times using different computation parameters, and a voting algorithm selects the best solution based on a given starting set of possible solutions. Their technique evaluates three-band sets of Kikuchi bands to generate a ranking of the most probable matches to different indexing solutions based on their frequency of occurrence. Unfortunately, this algorithm assumes that the true solution is given in the initial small set of provided possible solutions and only ranks the different possible solutions. No probabilistic measurements or statistical confidence data are included in the analysis. Thus, one must rely on the selected indexing solution without knowing how reliable the data may actually be. Any further analyses or calculations based on an unreliable indexing solution will also be unreliable, and a reviewer may not know that the results are unreliable.

Advantageous would be a method that determines automatically and unambiguously the crystalline phase and crystallographic characteristics of a specimen without the need for extensive sample preparation or sample destruction. Additionally, advantageous would be a method that can unambiguously determine the crystalline phase without knowing a priori what the crystalline phase might be.

SUMMARY OF THE INVENTION

According to the present invention, a method of determining the crystalline phase and crystalline characteristics of a sample is provided, comprising the steps of obtaining a backscattered electron Kikuchi pattern of a sample, determining line angles from said backscattered electron Kikuchi pattern, calculating line angles from crystallography data of selected compounds, and matching said line angles from said crystallography data with said line angles from the backscattered electron Kikuchi pattern to identify the crystalline phase and crystalline characteristics of the sample. Compounds that are possible solutions are selected from the database by comparing d-spacings, unit cell volumes and chemical composition information from the sample with data from the database. The crystalline phase is unambiguously identified by the method of the present invention. The sample can be of any crystalline phase symmetry.

The method of the present invention additionally includes the steps of calculating a backscattered electron Kikuchi pattern that would appear on a detector for the sample using the line angles calculated from the database crystallography data for the identified matched phase, correcting for sample orientation by using calibration data, and comparing the backscattered electron Kikuchi pattern of the sample with the calculated backscattered electron Kikuchi pattern using the line angles calculated from the database crystallography data to confirm the determination of the crystalline phase and crystalline characteristics of the sample.

The present invention also provides an apparatus for determining crystallographic characteristics of a sample, comprising an electron beam generator for generating an electron beam, an image collection system for obtaining an backscattered electron Kikuchi pattern of a crystalline particle of a sample, said pattern being produced by the illumination of said sample by said electron beam, and means for processing said backscattered electron Kikuchi pattern to obtain a unique indexing solution for said crystalline particle, said means for processing being in data communication with said image collection system.

BRIEF DESCRIPTIONS OF THE DRAWINGS

DETAILED DESCRIPTION OF THE INVENTION

Figure 1:
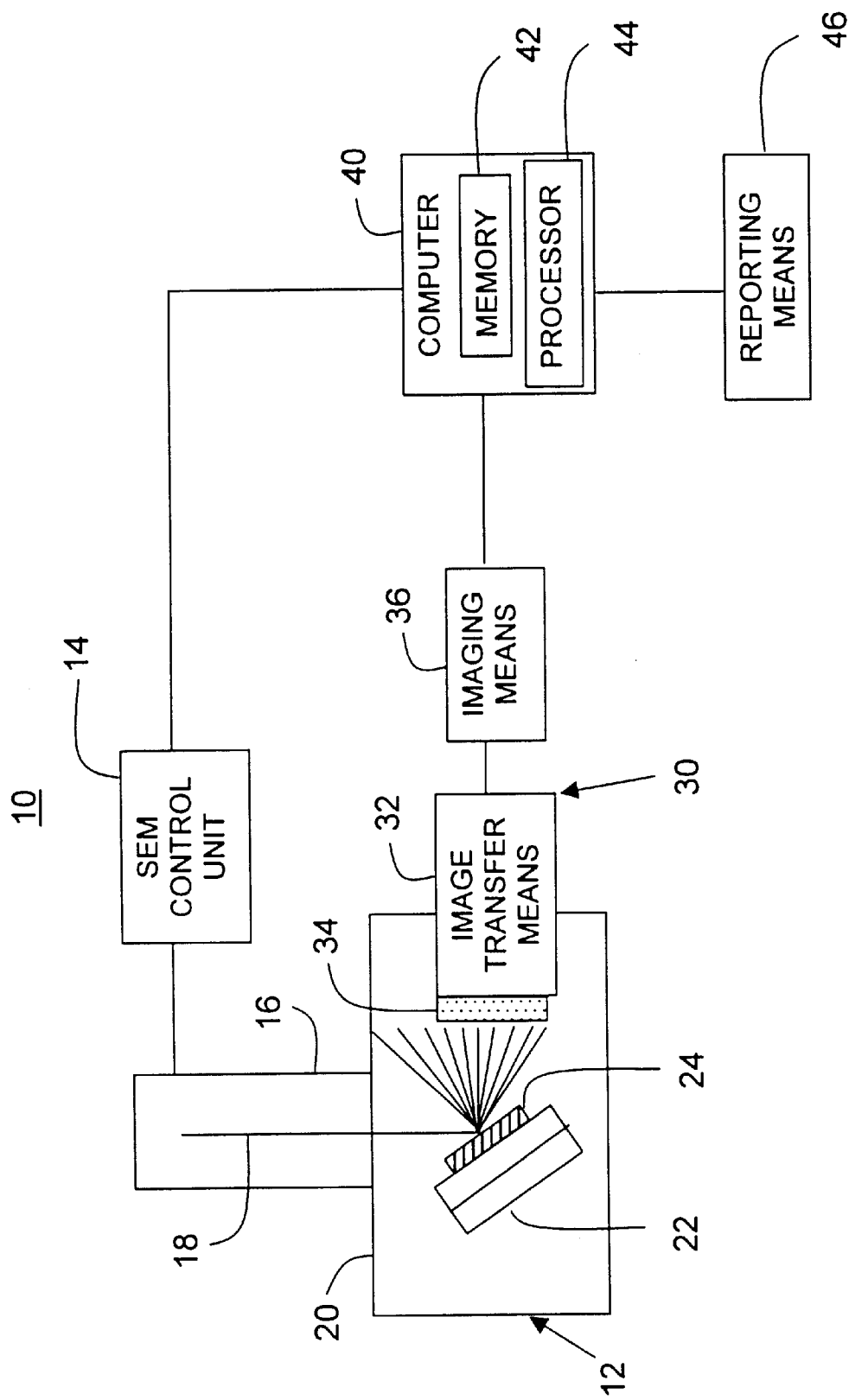
FIG. 1 shows a block diagram of one embodiment of the method of the present invention.

The present invention provides a single apparatus and method to quickly and automatically obtain material phase and crystallographic information of a sample. This information is often necessary to understand and perfect fabrication processes and to identify root causes for component failures. The present invention provides microstructural, morphological, elemental, orientation, and phase information, all from a single apparatus or instrument. In one embodiment, the present invention, utilizing almost any commercially available scanning electron microscope (SEM), can automatically and cost effectively identify the crystalline phases of a sample being investigated.

The present invention unequivocally identifies micron and sub-micron sized phases on or in a sample. The apparatus and method of the present invention does not merely identify the most probable phase or a set of probable phases but, importantly, determines the identity of the unknown phase of the particle under study on the sample and, furthermore, validates the phase selection. An important part of the invention is that the crystalline phase is unambiguously identified from an arbitrarily large set of possible crystalline phases in established databases.

Among other uses, the present invention can be utilized a) to identify phases on fracture surfaces of failed components, b) to study weld cracking and failure, c) to characterize the phases that form in brazing and welding of dissimilar metals and d) for particulate identification and characterization of semiconductors, minerals, and other structured materials.

The principal applications of the present invention generally relate to the complete phase characterization of micrometer and sub-micrometer sized areas in a specimen. These areas may be intrinsic to the sample, for example a phase that forms during the welding of stainless steels, or perhaps a particulate on a sample surface or dispersed on a substrate. The sample can be examined with a minimal amount of disturbance, a goal that becomes a requirement in fields where preserving the original sample is a necessity (e.g. forensics, failure analysis).

The capability to determine the phases present is very important in the field of failure analysis. Failure analysis is the study of component failures, either in test or in service. The failure can be an actual fracture of a component or may be a failure of the component due to corrosion or another root cause. The first step in understanding how a failure occurred is to observe the failed component and to determine what might have caused or contributed to the failure. The advantage of doing phase identification using the present invention is that, for the first time, the capability exists to look directly at fracture surfaces, determine the constituents present on the fracture surface, and relate these phases to the failure of the component. The present invention provides the only technique that can identify, with complete certainty, sub-micrometer sized phases on a fracture surface.

The present invention can also identify phases deposited or growing on surfaces or substrates. In the production of semiconductor devices, limiting the particulate contamination is very important during the production process. Once a processing failure related to particulate contamination has occurred, one of the most important functions is the identification of the nature of the particulate to try to understand how it got onto the device. In the past, this would have been accomplished by placing the integrated circuit in a scanning electron microscope and attempting to identify the particle using only chemical information. Unfortunately, there are many sources of contamination that have very similar chemistry, but different crystal structures. In these cases, the identification of the crystal phase, as can be accomplished by the present invention, is critical to understanding the problem and rectifying it. Other potential uses include in situ phase analysis and investigation of the mineralogy on other planets.

The present invention can also be applied to the solution of mineralogical or chemical synthesis problems. Many times minerals will be dispersed as particles or will be present in trace amounts only. The present invention has the capability to determine the mineral phases present in small isolated areas, and to do so in the presence of large quantities of other minerals. This is very valuable for mineralogical studies and can replace the scanning electron microprobe that only can infer the phases present by making quantitative elemental measurements.

A schematic of an apparatus 10 for indexing crystal lattice planes of a sample and uniquely identifying crystal phase and crystallographic information according to the present invention is shown in FIG. 1. According to one embodiment, apparatus 10 incorporates a conventional scanning electron microscope (SEM) 12. However, those skilled in this art will recognize that apparatus 10 may utilize a transmission electron microscope (TEM); however, use of a TEM requires sample preparation which can be time consuming and difficult. SEM 12 includes a SEM control unit 14 that controls an electron beam generator 16. Under the direction of SEM control unit 14, electron beam generator 16 discharges a focused electron beam 18 into a vacuum chamber 20. A holding stage 22 is mounted in vacuum chamber 20 such that a material sample 24 mounted thereon is bombarded or illuminated by electron beam 18.

An image collection system 30 is utilized to collect images of backscattered electrons diffracted form sample 24. Image collection system 30 includes a screen 34 that is coated with a scintillating material such as phosphorus. Screen 34 is coupled to an imaging means 36, such as a charge coupled device (CCD) based camera or a high-resolution video camera, and preferably a CCD based camera, through an image transfer means 32, preferably a fiber optic bundle or lens system. Screen 34 luminesces in accordance with the pattern of diffracted electrons falling thereon. The resulting electron backscatter diffraction patterns or backscattered electron Kikuchi patterns (BEKPs) are captured by the imaging means 36, where they are converted to electronic signals and converted into digital data.

A computer 40 controls the determination of the crystal indexing of the sample 24, as described subsequently. Computer 40 is a conventional computer desirably having as much computing power as is economically practical. Computer 40 includes conventional computer components, including a memory 42 and a processor 44. Memory 42 stores programming instructions that define various processes and algorithms carried out by processor 44 and other components of apparatus 10. In addition, memory 42 stores data, both alphanumeric and graphic, generated by the operation of apparatus 10.

Computer 40 controls the movement of holding stage 22, preferably through the SEM control unit 14. Through control of holding stage 22 and electronic steering of electron beam 18, a wide area of specimen 24 may be illuminated by electron beam 18 with backscattered electrons falling upon screen 34. Computer 40 may be coupled to a reporting means 46 that produces a report associated with the crystalline particles associated with sample 24. For purposes of this description, a report may include a crystal orientation image, a crystal phase map, a specimen grain size map, a BEKP or other information describing crystallographic characteristics. Reporting device 46 may be a video display terminal, a printer, or other device that may serve to convey information related to the crystals or crystalline particles in or on sample 24.

This apparatus is used to collect a backscattered electron Kikuchi pattern for a particle on a sample and provides the means according to the method of the present invention for processing the BEKP to obtain a unique indexing solution for the crystalline particle under study and therefore identifies the previously unknown phase of the particle. This identification is unambiguous and is not merely a most probable solution.

The backscattered electron Kikuchi patterns used by the apparatus of the present invention are obtained by illuminating a highly tilted specimen with a narrow stationary electron beam. Within the specimen, the electrons are elastically and inelastically scattered, with some of the electrons being scattered out of the specimen. The elastically scattered electrons (diffracted electrons) generate the Kikuchi diffraction pattern used by the present invention for unambiguous determination of the crystalline phase.

Figure 2:
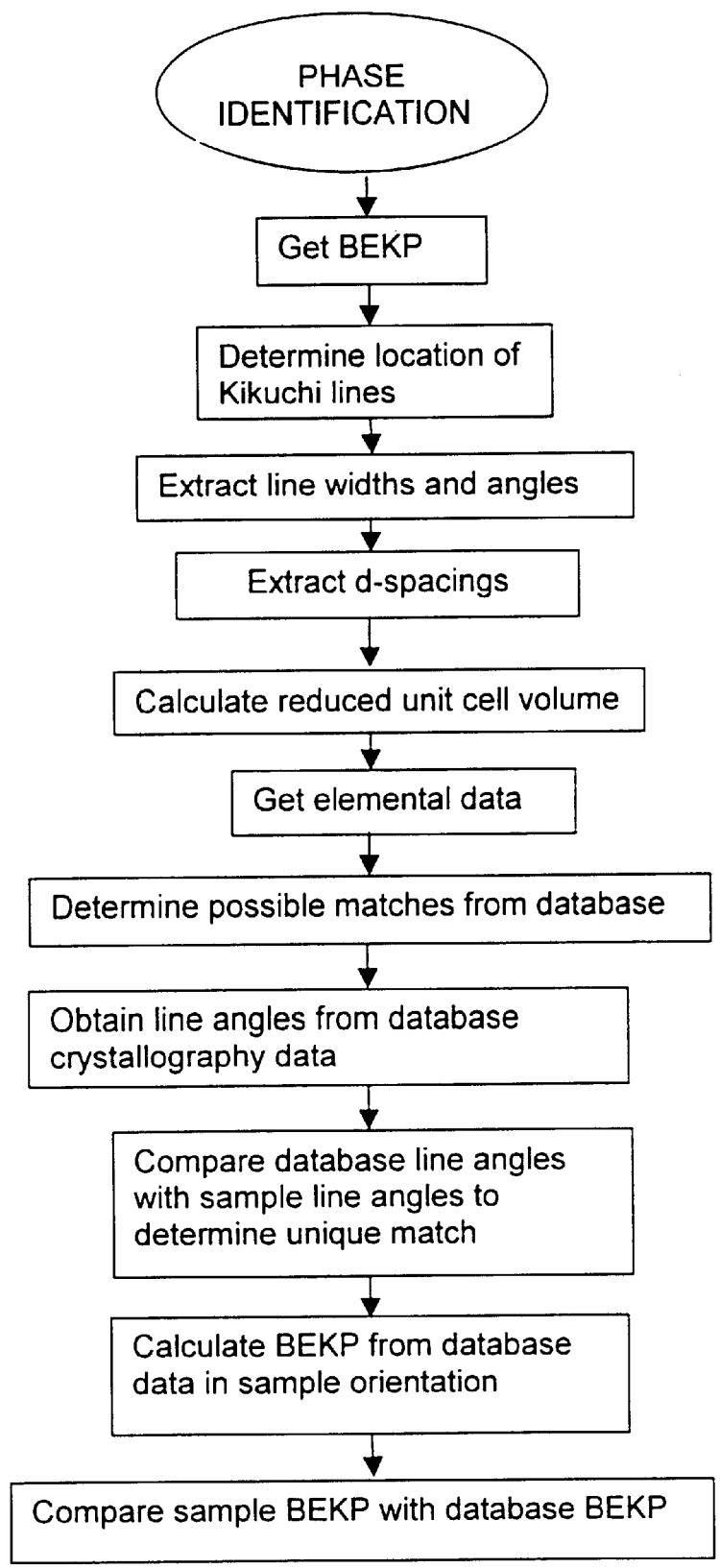
FIG. 2 shows the general block diagram showing the method for determining phase characteristics of a sample.

The method for uniquely determining the phase and crystallographic parameters of a sample according to the present invention is given in the block diagram of FIG. 2.

The backscattered electron Kikuchi patterns used by the apparatus of the present invention are obtained by illuminating a highly-tilted specimen with a narrow stationary electron beam. In one embodiment, an SEM is used to produce the electron beam. Within the specimen, the electrons are elastically and inelastically scattered, with some of the electrons being scattered out of the specimen. The elastically scattered electrons (diffracted electrons) generate the Kikuchi diffraction pattern used by the present invention for unambiguous determination of the crystalline phase. Kikuchi bands or lines intersect each other at various points.

It is not necessary to have a detailed understanding of the physics of electron scattering to use these patterns for phase identification, but it should be noted that the intensities of the resulting Kikuchi lines are proportional to the atomic structure factors to the second power and do not vary significantly as the orientation of the region being investigated changes. This insensitivity of the intensity to changes in orientation is an important property that allows the present invention to be easily applicable to crystallographic phase analysis.

A modification of standard algorithms, such as a Hough transform, is used to identify the Kikuchi lines from the Kikuchi pattern and determine the location of the lines on the backscattered electron Kikuchi pattern (BEKP). The Hough transform uses the slope and intercept of the Kikuchi lines from a reference point in the BEKP to identify the location of the lines as points. The modification of the transform uses a cylindrical coordinate transformation to utilize the angle and distance of the lines from the reference point to identify the line locations. These lines correspond to the pattern of backscattered electrons coming through the atomic planes. The width of these lines is inversely related to the spacing of the atoms within the plane associated with the line or band. In order to achieve maximum data utilization, the Hough transform data is normalized as a function of line length. This process avoids the tendency of the Hough transform to reveal shorter lines as lower intensity spots. However, the normalized data from the Hough transform is not sufficient to provide an accurate measurement of the d-spacings. The use of normalized data, along with algorithms which use the Hough transform data as a starting point for the processing of the original BEKP image, are an important part of the method of the present invention. Specifically, the Hough transform provides a starting band that is iteratively rocked in angle orientation, and adjusted in width, until an optimal overlay of the original pattern is achieved. This process has the additional advantage that erroneous data generated by the Hough transform is captured since the band overlay will wander outside acceptable limits. In this manner, angles between planes, zone axis locations, and, importantly, d-spacings can be obtained to an accuracy far better than that achievable with standard Hough transform techniques. Values of d-spacings are generally obtained that are within approximately 5% of the values as determined by x-ray diffraction.

Based on the knowledge of these crystallographic parameters, particularly d-spacings and angles between planes, a reduced unit cell volume is calculated. The actual unit cell volume may be an integral multiple of the reduced unit cell volume. In order to calculate the unit cell volume, the reciprocal space information from the diffraction pattern is first converted to real space by the use of standard equations. Once this conversion is performed, the unit cell volume is calculated by using the reflections in the pattern in groups of three. The unit cell volume is the volume enclosed by planes located at the measured d-spacings apart in space with the measured angles from the diffraction pattern between them. Once all possible combinations have been calculated the largest common multiple is calculated. This value is the value used in the subsequent database search.

Elemental data is collected about the sample using standard diagnostic techniques, and preferably an energy dispersive x-ray spectroscopy (EDS). EDS provides no information on crystal structure or phase. However, from the combination of the elemental data, the crystallographic parameters and unit cell volume, the database is searched to determine a set of possible matches, given an error tolerance specified by the user of the method. The method of phase identification of the present invention utilizes the International Centre for Diffraction Data (ICDD) database containing over 100,000 inorganic phases to provide an unambiguous phase determination (other similar databases could be used but this database is the recognized standard for those skilled in the art). The ICDD database contains, among other information, the name of the phase, the chemical formula, the unit cell volume, and the indices, d-spacings, and intensities of the band reflections. The elemental data obtained from the EDS limits the potential matches to only those phases that contain the specified elements. The values of the determined reduced unit cell volume of the sample and the indices and d-spacings of the Kikuchi bands further constrain the search to determine a set of possible matches. The number of possible matches returned by the algorithm depends on variables that include the tolerance error specified and the accuracy of the composition data, the unit cell volume and d-spacings provided.

The unit cell volume is determined in the following manner. Once the locations of the bands in the image are located the angles between the bands and the width of the bands can be determined. An arbitrary unit cell is then defined as any three d-spacings and the angles between the planes that correspond to those d-spacings. In any given pattern there are normally at least 7 bands found. When these 7 bands are taken three at a time, there are a large number of unit cells that can be determined. Once all of these unit cell volumes are determined the largest multiple is determined. The database is then searched on the basis of multiples of this volume.

The crystallographic information on the set of possible matches from the database is compared with the crystallographic information from the sample. Importantly, an algorithm of the present invention calculates all possible permutations of angles between all pairs of planes of the Kikuchi bands from each of the possible matches from the database search and determines which phase matches the Kikuchi band angles obtained from measurements on the sample. The algorithm selects a Kikuchi band and calculates the angles of the planes based upon that band. The algorithm then uses the crystallographic data from each possible match from the database to calculate all possible permutations of Kikuchi band angles. A unique match is obtained as the phase of the sample has a Kikuchi pattern wherein the angles of the planes form a unique set. When the angles of the planes of a phase selected form the database match the angles of the planes of the sample, that phase is uniquely determined to be the phase of the sample. This algorithm thus described provides the means to determine the Kikuchi bands of the phase or compound from the database that matches the Kikuchi bands from the sample.

A validation step is then performed wherein the crystallographic information of the identified unique phase is processed to calculate a Kikuchi pattern in the exact orientation of the sample and system apparatus on which the measurements were made. To calculate this Kikuchi pattern, data on the distance from the detector to the sample and the pattern center are used. These data are obtained from a calibration algorithm wherein a sample of known phase is analyzed and the determined Kikuchi bands are compared with crystallographic data from the database on the known phase and the orientation parameters adjusted to give a visually exact match between the Kikuchi pattern determined from the sample and the Kikuchi pattern determined from the database information. When these orientation parameters have been determined, they are used with the database crystallographic information to calculate and generate the lines of a Kikuchi pattern for the crystal phase selected as a match for the sample. This generated Kikuchi pattern is overlayed on the Kikuchi pattern determined from the sample, with both patterns in the same physical orientation with respect to the measuring apparatus or system. Both graphical and tabular data formats are available to make these comparisons. If the phase identification is correct, then the two patterns will have Kikuchi band locations and angles between bands that are essentially identical. This pattern matching can be done visually or electronically. If the two patterns do not match, then the algorithm checks the other possible matches to determine if another database compound has Kikuchi bands that match the Kikuchi bands of the sample and then proceeds again with the validation step to determine if the match is correct.

In order to perform accurate phase identification, the camera must be carefully calibrated. There are a number of schemes in the literature to accomplish this. Most involve either moving the camera or using the precise tilt of a known sample to determine the camera center and the distance from the specimen to the imaging screen. In the present invention, we have devised a calibration technique that uses only a pattern from a known material, preferably Si, in any random orientation. Once the pattern from the known material is obtained, the pattern is analyzed using the Hough transform and then the positions of the Kikuchi bands are determined. The calibration space is then searched until a set of calibrations (pattern center and camera length) is found that permits the angles between the planes found in the calibration image to accurately match the accepted values from the data base. This technique is quick and accurate.

Importantly, this algorithm process will identify the phase of a sample and therefore subsequent crystallographic data, for a sample of any symmetry.

EXAMPLE 1

In one example, a sample, known to be arsenopyrite, was mounted in the scanning electron microscope with the surface to be analyzed at a high angle to the electron beam. A Kikuchi pattern was then obtained along with the elemental chemical composition. The elemental chemical data showed that the sample contained arsenic, iron, and sulfur.

The line positions were determined and the reduced crystal volume calculated to be 35.5. The input for the ICDD database search included the elemental chemical data (arsenic, iron, and sulfur), the line positions, and the reduced crystal volume. The search required that the database matches contain the identified chemical elements, i.e., arsenic, iron, and sulfur, and have a reduced cell volume that is a multiple of 35.5; an allowable search error, in this example 10%, is specified. In this example, the algorithm showed that only one possible match existed in the database. The possible match was AsFeS with a unit cell volume of 174.10, a very close multiple of 5 of the unit cell volume calculated from the pattern. The pattern was then indexed automatically by the software and, as a visual validation of the selection, a Kikuchi pattern was simulated using the crystallographic information from the database and the crystal orientation calculated from the pattern. Excellent visual agreement was obtained between the experimentally obtained Kikuchi pattern and the Kikuchi pattern generated from the database information from the crystal phase selected as the match for the experimental data collected, providing a visual demonstration that the identity of the crystal phase was indeed AsFeS.

EXAMPLE 2

A particle was growing on the surface of non-volatile memory component which, when completed, was meant to be part of an integrated circuit. This unwanted crystal growth was occurring during the deposition of a ruthenium film barrier on a single crystal silicon substrate. These undesired crystals, though quite small and very sparsely distributed, were large enough to make the completed device fail. The small area fraction of these particles precluded the use of X-ray diffraction or transmission electron microscopy as analysis tools. However, it was still necessary to identify them in order to learn if it would be possible to modify the processing parameters to produce a defect-free ruthenium coating. The apparatus of the present invention successfully identified these widely scattered particles as ruthenium dioxide.

The Kikuchi pattern was obtained. The reduced unit cell volume was calculated to be 28.6, which is nearly an even multiple of the actual unit cell volume for $RuO_2$ of 62.9. The EDS analysis determined that the particles consisted of ruthenium and oxygen. A search of the database determined that the set of possible matches included only 2 ruthenium oxides. The pattern is then indexed automatically by the software to demonstrate that the database selection $RuO_2$ is a match to the sample. Finally, as a visual validation of the selection, the pattern is simulated using the crystallographic information from the database and the crystal orientation calculated from the pattern. Excellent agreement between the simulated pattern and the pattern determined from the sample demonstrated the identity of the crystal phase to be ruthenium dioxide. With that information in hand the process developers were able to lower the temperature for the deposition of the ruthenium barrier and completely avoid the formation of the ruthenium dioxide crystals.

The invention being thus described, it will be apparent to those skilled in the art that the same may be varied in many ways. Such variations are not to be regarded as a departure from the spirit and scope of the invention, and all such modifications are intended to be included within the scope of the following claims.

We claim:

1. A method for determining the crystalline phase and crystalline characteristics of a sample, comprising:
    obtaining a backscattered electron Kikuchi pattern of a sample;
    determining line angles from said backscattered electron Kikuchi pattern;
    obtaining line angles from crystallography data of selected compounds; and
    matching said line angles from said crystallography data with said line angles from the backscattered electron Kikuchi pattern to identify the crystalline phase and crystalline characteristics of the sample.

2. The method of claim 1 wherein the sample can be of any crystalline phase symmetry.

3. The method of claim 1 wherein the backscattered electron Kikuchi pattern is obtained using a scanning electron microscope.

4. A method for determining the crystalline phase and crystalline characteristics of a sample, comprising:
    obtaining a backscattered electron Kikuchi pattern of a sample;
    determining the location of lines on said Kikuchi pattern;
    extracting from the Kikuchi pattern widths and angles of said lines;
    extracting d-spacings of said lines;
    determining an approximate unit cell volume;
    obtaining chemical composition information about the sample;
    determining compounds from a database that match the chemical composition information and approximate unit cell volume, said database containing crystallography data;
    obtaining line angles of said matched compounds from the database crystallography data; and
    comparing said line angles calculated from the database crystallography data for said matched compounds with the angles extracted from the Kikuchi pattern of the sample to identify a phase match and determine the crystalline phase and crystalline characteristics of said sample.

5. The method of claim 4 wherein the chemical composition information is obtained using energy dispersive x-ray spectroscopy.

6. The method of claim 4 wherein the backscattered electron Kikuchi pattern is obtained using a scanning electron microscope.

7. The method of claim 4 wherein the location of the lines on said Kikuchi pattern is determined using a Hough transform modified to use a cylindrical coordinate system and further modified wherein the Hough transform data is normalized as a function of line length.

8. The method of claim 4 wherein the d-spacings obtained are within approximately 5% of the values obtained using x-ray diffraction.

9. The method of claim 4 further comprising the step of specifying a tolerance error in determining compounds from the database that match the chemical composition information and approximate unit cell volume.

10. The method of claim 4 wherein said database crystallography data comprises composition information, unit cell volumes, and d-spacings of known crystalline phases.

11. The method of claim 4, further comprising the steps of:

generating a second backscattered electron Kikuchi pattern that would appear on a detector for the sample using the line angles obtained from the database crystallography data for the identified matched phase, correcting for sample orientation by using calibration data; and generating a confirmation signal, comprising comparing the backscattered electron Kikuchi pattern of the sample with the calculated backscattered electron Kikuchi pattern using the line angles obtained from the database crystallography data to confirm the determination of the crystalline phase and crystalline characteristics of the sample.

12. An apparatus for determining crystallographic characteristics of a sample, comprising:

an electron beam generator for generating an electron beam;

an image collection system for obtaining an backscattered electron Kikuchi pattern of a crystalline particle of a sample, said pattern being produced by the illumination of said sample by said electron beam; and means for processing said backscattered electron Kikuchi pattern to obtain an indexing solution for said crystalline particle, said means for processing being in data communication with said image collection system and comprising an algorithm to obtain said backscattered electron Kikuchi pattern of said sample, to determine the location of the lines on said Kikuchi pattern, to extract from the Kikuchi pattern line widths and angles of said lines, to extract d-spacings of said lines, to determine an approximate unit cell volume, to obtain chemical composition information, determine compounds from a database that match the chemical composition information and approximate unit cell volume, said database containing crystallography data, to calculate line angles of said matched compounds from the database crystallography data, and to compare said line angles calculated from the database crystallography data for said matched compounds with the angles extracted from the Kikuchi pattern of the sample to identify a phase match and determine the crystalline phase and crystalline characteristics of said sample.

13. The apparatus of claim 12 wherein the electron beam generator is part of a scanning electron microscope.

14. The apparatus of claim 12 wherein the image collection system includes a screen coated with a scintillating material.

15. The apparatus of claim 14 wherein said screen is coupled to a charge coupled device based camera to obtain high resolution backscattered electron Kikuchi patterns.

* * * * *